United States Patent [19]
Schiek, Sr.

[11] Patent Number: 6,053,883
[45] Date of Patent: Apr. 25, 2000

[54] SUPPORT AND UTILITY BELT

[76] Inventor: James W. Schiek, Sr., 513 B Saratoga Ave., Fond du Lac, Wis. 54935

[21] Appl. No.: 08/290,678

[22] Filed: Aug. 15, 1994

Related U.S. Application Data

[63] Continuation of application No. 08/023,300, Feb. 26, 1993, abandoned, which is a continuation of application No. 07/728,742, Jul. 12, 1991, abandoned.

[51] Int. Cl.[7] ........................................................ A61F 5/00
[52] U.S. Cl. .............................................................. 602/19
[58] Field of Search ............................... 482/106; 2/311, 2/312, 338, 42, 44; 602/19; 128/96.1, 99.1, 100.1, 101.1, 111.1, 115.1

[56] References Cited

U.S. PATENT DOCUMENTS

| | | | |
|---|---|---|---|
| 1,600,027 | 9/1926 | Welsand | 224/904 |
| 2,185,834 | 1/1940 | Creper | 450/155 |
| 3,052,236 | 9/1962 | Schreiber | 602/13 |
| 4,175,553 | 11/1979 | Rosenberg . | |
| 4,685,668 | 8/1987 | Newin, Jr. | 482/106 |
| 4,745,911 | 5/1988 | Bender | 482/106 |
| 4,905,993 | 3/1990 | Barone | 482/106 |
| 4,964,401 | 10/1990 | Taigen | 482/106 X |

*Primary Examiner*—Linda C. M. Dvorak
*Attorney, Agent, or Firm*—Bracewell & Patterson

[57] ABSTRACT

A support belt has a back support pad and an abdominal support pad for supporting both the back and abdomen during strenuous activity. The support pads are secured to one another by belt side portions which are of a vertical height which provides clearance between the ribs and hips of the wearer, maximizing abdominal and back support with a minimum of discomfort. Utility rings may be secured to the belt for attaching harnesses and the like to assist with support during strenuous activity.

11 Claims, 2 Drawing Sheets

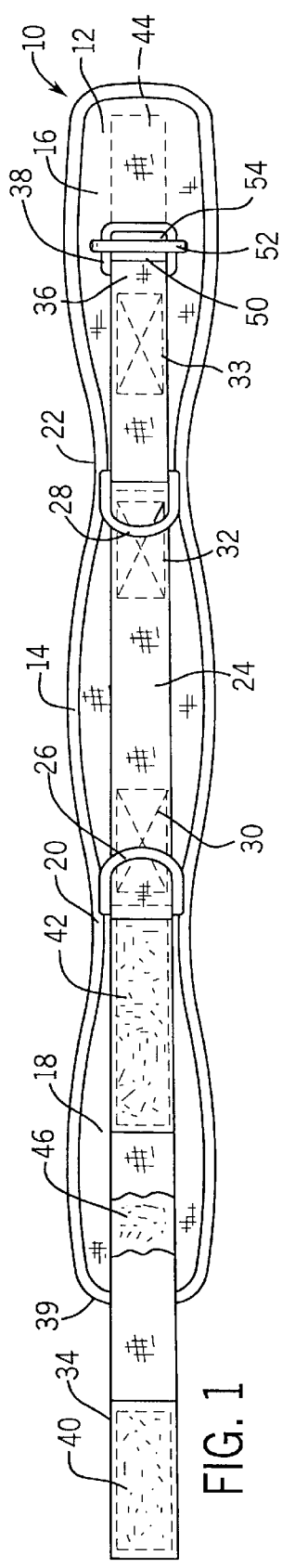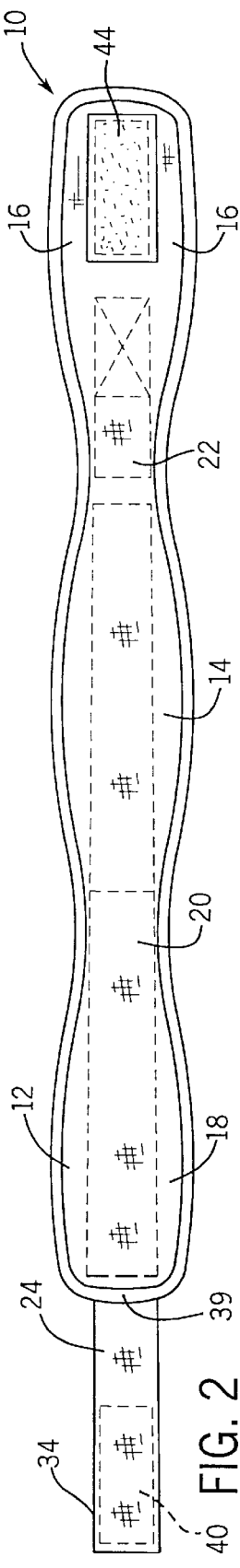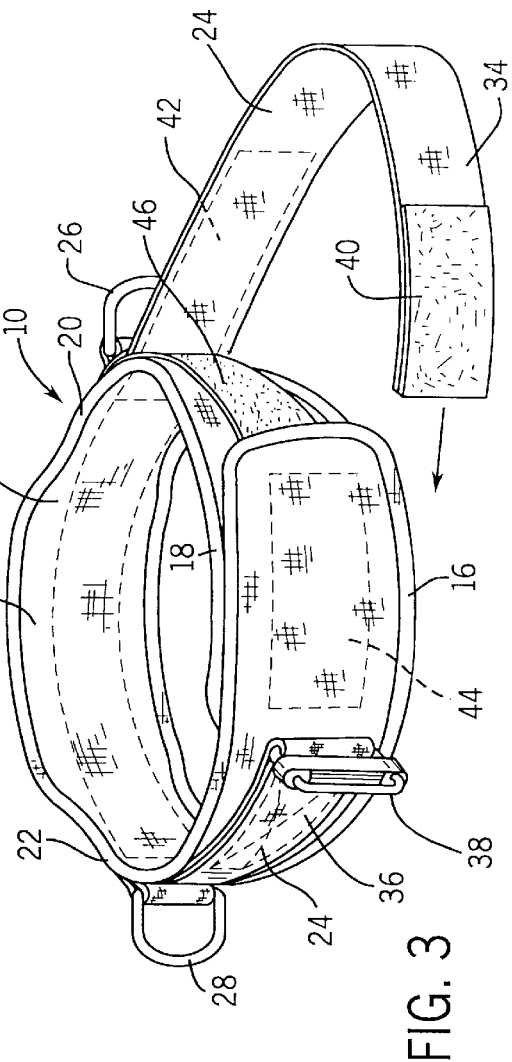

SUPPORT AND UTILITY BELT

CROSS-REFERENCE TO RELATED APPLICATIONS

This is a Continuation of application(s) Ser. No. 08/023, 300 filed on Feb. 26, 1993 now abandoned which is a continuation of application Ser. No. 07/728,742 filed on Jul. 12, 1991, now abandoned.

This application is related to my co-pending application Ser. No. 07/491,349 entitled "SUPPORT DEVICE" filed on Mar. 9, 1990; and application Ser. No. 07/665,990 entitled "BELT SUPPORT DEVICE WITH ADJUSTABLE HOOK AND LOOP-TYPE FASTENER" by James W. Schiek, Sr. and James M. Schiek filed on Mar. 7, 1991.

BACKGROUND OF THE INVENTION

1. Field of the Invention

The subject invention is directed to belts for providing both back and abdominal support and is particularly directed to a utility belt having an enlarged back pad, an enlarged abdominal pad and reduced side sections between the rib and hip of the wearer.

2. Description of the Prior Art

Support belts have been available for many years to provide back support when lifting or moving heavy objects. An outgrowth of the support belt is a utility belt which permits a harness to be attached directly to the belt to aid in the lifting or moving motion and activity. Also, utility belts have been very useful in providing a means for attaching a safety harness to the wearer for a variety of tasks such as, by way of example, window washing of tall buildings and the like.

Such belts have also become common in certain types of sports and activities. For example, body builders and weight lifters have long used support belts to provide additional support protecting the back against injury during body building exercises. Also, such belts have been very useful in providing an added measure of safety when using harness-type tree stands for bow hunting and the like. An example of a belt specifically designed for weight lifting and body building is shown in my co-pending application Ser. No. 07/491,349 entitled "SUPPORT DEVICE" filed on Mar. 9, 1990.

Recently, it has become mandatory in a number of states that invalid care personnel use "GAIT" belts placed around the waist of the patient before ambulating, transferring or lifting a patient. This permits the care giver to move the patient by sliding the hands upward under the belt with the palms facing away from the patient and grasping the belt securely. While this provides additional protection to the patient, it has been found that this type of lifting motion creates additional strain on the back of the care giver. By providing the care giver with a back support device such as a support belt, the strain has been reduced.

Most scientific literature agrees that such belts can help prevent back injuries. See for example the article, "Why Use Belts" by Jeffrey E. Lander, Ph.D., pages 72, 73 Body Building Lifestyles, April 1991. See also Strength-Power Update, Vol. 1, No. 3, Summer 1986 published by the National Strength Research Center.

The effectiveness of weight belts during squat exercises and the like is discussed in "The Effectiveness of Weight Belts During the Squat Exercise" by Jeffrey E. Lander, R. Leslie Simonton and Joel K. F. Giacobe of the Biomechanics Laboratory, Department of Health and Human Performance, Auburn University. This article was published in Medicine in Science and Sports Exercise, Vol. 22, No. 1, pps. 117–126 by the American College of Sports Medicine, 1990. The article discusses the effectiveness of weight belts during the performance of the parallel squat exercise. The data generated during these tests supports a position that a weight belt can aid in supporting the body trunk of the wearer by increasing intra-abdominal pressure. In fact, a tight fitting weight belt can increase the intra-abdominal pressure by up to 40% over wearing no belt. This means that a body builder who possesses very strong abdominals will benefit from wearing a weight belt. Wearing the belt increases the intra-abdominal pressure, decreasing the forces acting directly on the lumbar spine by up to 50%. This is important because the compressive forces on the lower spine can exceed 2500 pounds during a 300 pound squat.

In other types of activities, it has been found that the weight belts do reduce the load on the spine and provide for a greater degree of protection. While this is very important for body builders, it is also extremely beneficial for other strenuous activities particularly in the work place where the wearer is required to do heavy lifting and moving activities. In addition to increasing the intra-abdominal pressure, thereby reducing the strain on the back and protecting the back against injury, it has been found that use of the belt also reduces the fatigue factor of the wearer when used in industrial environments where heavy lifting and strenuous moving activity is undertaken over an extended period of time.

SUMMARY OF THE INVENTION

While the various belts available in the prior art are beneficial in providing good back support to the wearer during strenuous activity, none of the belts combine back support with increased abdominal support to provide maximum intra-abdominal pressure and maximum benefits in reducing the strain on the wearer. The subject invention is directed to a belt specifically designed to provide back support in combination with increased abdominal support. In addition, the belt of the subject invention is designed to provide ample clearance between the hips and ribs of the wearer, providing maximum comfort and maximum mobility while providing enhanced abdominal and back support.

In the preferred embodiment of the invention, the belt includes an enlarged back pad adapted to be placed against the lumbar musculature of the back for protecting the lumbar region and an enlarged abdominal pad to provide support against the abdominal wall and abdominal muscles of the wearer. The two pads are attached to one another by side sections which are of a reduced dimension at the waist of the wearer, providing clearance between the hips and the ribs, allowing bending and side-to-side motion without discomfort.

In the preferred embodiment of the belt, the pads and reduced sections are integral and are designed to be wrapped about the waist of the belt and held in place by an exterior strap which is tightened to the individual taste and needs of the wearer. Hook and loop type fastener pads may be used to hold the belt in place, in combination with sliding buckles to provide a tight secure and easy-to-use fastening system.

It is a feature of the belt that utility rings may be placed on the belt for securing the belt directly to a harness or implement which is to be moved or lifted by the wearer, providing added safety and providing the ability to use the trunk of the body to aid in the activity.

It is, therefore, an object and feature of the subject invention to provide for an improved weight belt which provides support to both the back and the abdominal wall of the wearer.

It is another object and feature of the subject invention to provide a belt which has enlarged back and abdominal support pads attached by reduced side pads for maximizing comfort and permitting maximum mobility to the wearer.

It is yet another object and feature of the subject invention to provide for a utility belt to which harnesses and other implements can be attached to aid in the wearer in performing strenuous activities.

It is yet another object and feature of the subject invention to provide for a belt having both good abdominal and back support which has a multiple fastening system for securely holding the belt on the wearer.

Other objects and features of the invention will be readily apparent from the drawings and detailed description of the preferred embodiment which follow.

BRIEF DESCRIPTION OF THE DRAWINGS

FIG. 1 is a plan view of a support/utility belt in accordance with the subject invention.

FIG. 2 is a reverse view of the belt of FIG. 1.

FIG. 3 is a perspective view of the belt of FIG. 1 shown in a configuration for encircling the waist of the wearer with the first attachment means in the secured position.

DETAILED DESCRIPTION OF THE PREFERRED EMBODIMENT

Figure 4:
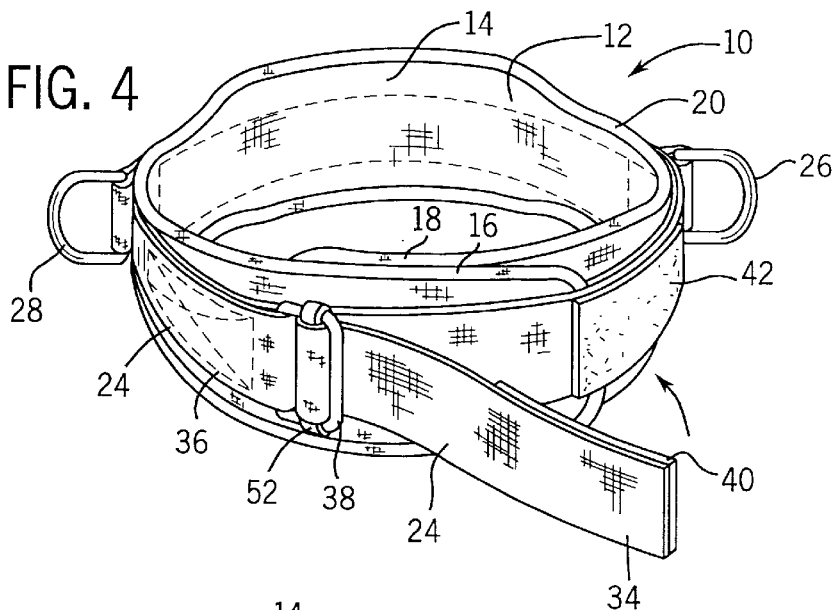
FIG. 4 is a view similar to FIG. 3, showing the belt with the second attachment means in the secured position.

A plan view of the belt 10 of the subject invention is shown in FIG. 1. As there shown, the belt comprises an elongate base 12 having an enlarged back pad 14 and two enlarged outer pads 16 and 18 joined with the back pad 14 by the reduced sections 20 and 22. In the preferred embodiment, the belt base 12 may comprise a sandwiched material made of a semi-rigid base such as, by way of example, a closed-cell vinyl nitryl, wrapped by a cloth or vinyl cover to provide additional comfort and to enhance the aesthetics of the belt. The semi-rigid base material provides substantially rigid back and abdominal support when the belt encircles the waist of the wearer, as is particularly shown in FIG. 5. The reduced sections 20, 22 are adapted to be placed between the hip bones and the lower rib at the sides of the wearer with the enlarged back pad providing a solid back support for the lumbar region and the enlarged pads 16, 18 being disposed over the abdomen of the wearer to provide good abdominal support. In the preferred embodiment, the support pads have a vertical height of approximately 5 inches, whereas the reduced sections are of a height of approximately three inches.

In the preferred embodiment of the invention, a strap 24 is secured to the exterior surface of the base 12 and includes a pair of harness rings 26, 28 secured between the strap 24 and pad 12 in the region of the reduced sections 20, 22, respectively. The strap is secured to the belt by suitable means such as the stitching pattern shown at 30, 32, and 33 and has loose free outer ends 34, 36. A standard sliding buckle 38 is suitably secured to the outer end 36 of the belt. The outer end 34 of the belt extends outwardly beyond the outer edge 39 of the enlarged abdominal pad 18 and includes fastener means such as the hook and loop type fastener pad 40 secured to the outer surface thereof. A complementary hook and loop type fastener pad 42 is secured to the outer surface of the strap adjacent the ring 26 and in the vicinity of the reduced section 20.

Figure 5:
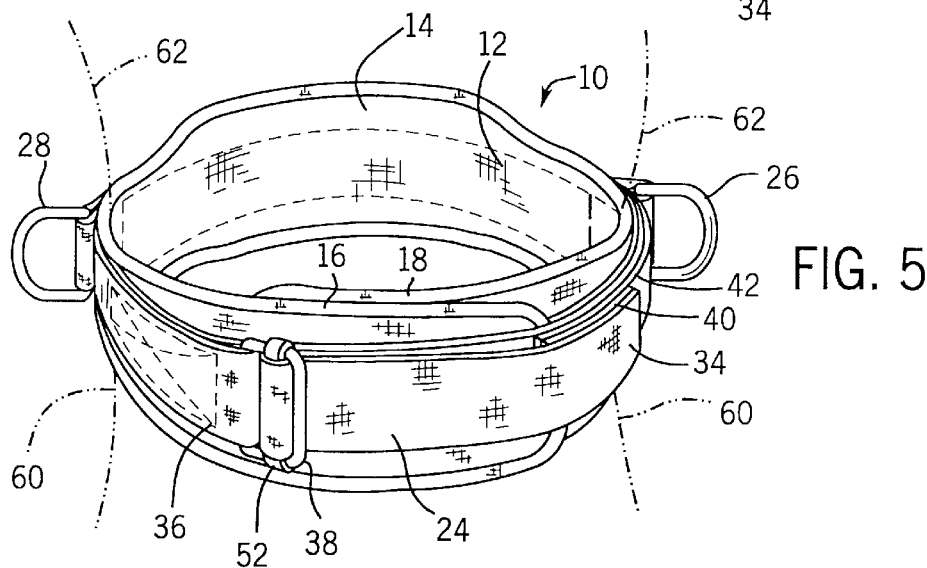
FIG. 5 is a view similar to FIG. 4, showing the belt strap in the stowed position.

As best shown in FIG. 2, the interior surface of the belt includes a hook and loop type fastener pad 44 secured to the rear surface of the base in the vicinity of the enlarged abdominal pad 16. This hook and loop type fastener pad is complementary with the hook and loop fastener pad 46 which is on the outside of the base 12 in the vicinity of the enlarged abdominal pad 18 (also see FIG. 3). As shown in FIGS. 3, 4, and 5, the belt is adapted to encircle the waist of the wearer and is first positioned as shown in FIG. 3 around the waist, with the abdominal pad 16 placed against the abdomen of the user and the abdominal pad 18 disposed outboard of the pad 16 and in overlying relationship therewith. The hook and loop fastener pad 44 is then placed against the fastener pad 46 for securing the belt in place.

To provide a tight securing relationship for securing the belt about the waist of the user, the outer end 34 of the strap 24 is then placed through the inner slot 50 of the slide buckle 38, as is shown in FIG. 4. The outer end 34 of the strap is then looped over the sliding member 52 of the buckle and back through the forward slot 54, after which the strap 24 can be cinched to tighten the belt about the waist of the user to the individual wearer's comfort. At this point, the belt is securely fastened to the wearer and will not be loosened until the strap 24 is removed by slipping it back through the buckle 38.

Figure 6:
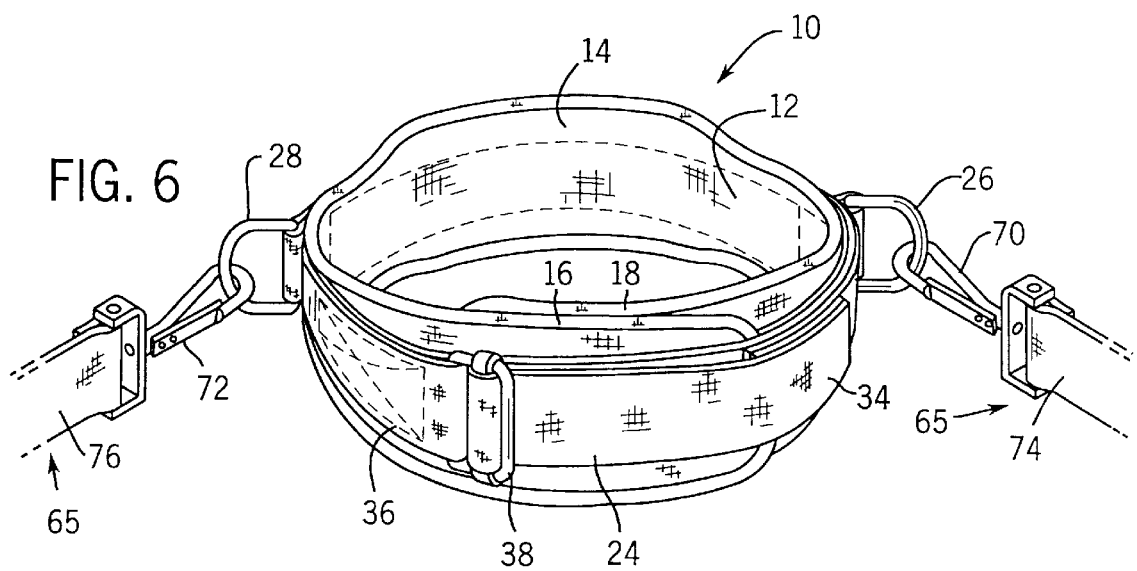
FIG. 6 is an illustration similar to FIG. 5, showing a typical harness attached to the belt.

The loose end 34 of the belt includes a hook and loop fastener pad 40 which is complementary with the hook and loop fastener pad 42 provided on the outer surface of the belt, for holding the loose strap end 34 against the belt, as shown in FIGS. 5 and 6.

As is particularly shown in FIG. 5, the belt is designed to provide both abdominal and back support by placing the enlarged abdominal pads 16, 18 against the abdomen of the wearer in the vicinity of the waist and the enlarged back pad 14 against the lumbar musculature of the back of the wearer in the lumbar region. The reduced side sections 20, 22 become the side areas of the belt when it encircles the waist, and are designed to be between the upper limit of the hip bones as shown in phantom at 60 (FIG. 5) and beneath the lowest ribs as shown in phantom at 62. This provides the maximum amount of movement for bending both backward and forward and side-to-side when the wearer has the belt securely fastened about the waist. This provides maximum secure support for both the back and abdomen while maximizing the comfort of the wearer.

The utility rings 26, 28 are disposed at the sides of the belt as defined by the reduced sections 20, 22 to distribute the forces on the belt evenly across the back and the abdomen. As shown in FIG. 6, the utility rings 26, 28 can be used to secure any of a variety of harnesses or straps 55 by using the clips 70, 72 secured to the outer ends 74, 76 of the harness. Thus, the utility belt of the subject invention maximizes the size of the support pads of the belt in both the abdominal region and the lumbar region of the back while minimizing discomfort by providing ample clearance between the hips and ribs of the wearer.

While specific embodiments and features of the subject invention have been described herein, it will be readily understood that the invention encompasses all modifications and enhancements within the scope and spirit of the claims appended hereto.

I claim:

1. A support belt adapted for encircling and being secured to the waist of a wearer for providing both back and abdominal muscle support during strenuous activity while providing a non-interfering support and a non-interfering fit with the skeletal structure of the ribs and hips of the wearer, the belt comprising:

a. an elongate base having a longitudinal axis and opposite outer ends and of a length sufficient to encircle the waist of the wearer, the base including an enlarged back support area and an enlarged abdominal support area, each area of a first fixed predetermined vertical height and each area being integral within the base, and made of a semi-rigid material wrapped in a flexible cloth for comfort, the areas being disposed within the base such that the areas are opposite one another when the belt is encircling the waist of the wearer;

b. reduced side areas within the base, having a second predetermined vertical height smaller than said first predetermined vertical height and disposed intermediately of the back support and abdominal support areas and opposite one another between the hips and ribs of the wearer when the belt is encircling the waist, said reduced side areas being sized to allow the belt to be sufficiently tightened against the back and abdominal walls without encountering the skeletal structure of the ribs or hips of the wearer thereby evenly distributing and providing optimum support to both the back and abdominal walls and accommodate bending and side-to-side motion of the wearer;

c. a first fastening means comprising a first pad portion at one end of the base and a second pad portion disposed at the other end of the base, the first and second pad portions adapted to be placed in overlying, releasably secured relationship with one another when the belt is encircling the waist of the wearer;

d. an elongate strap of flexible, generally non-stretchable material secured to and coaxial with the base, and having free opposite ends;

e. a second, cinchable fastening means on the strap comprising a fastener secured to one of said strap ends and a flap on the other end adapted to be received in and secured by said fastener and cinched to fit when the belt is placed around the waist of the wearer; and f. means for securing the first fastening means after the belt is properly cinched.

2. The support belt of claim 1, wherein the first and second pad portions at the ends of the base define an abdominal support pad and the back support area further defines a back support pad.

3. The support belt of claim 2, wherein the abdominal support pad portions, when in overlying relationship with one another, have abutting surfaces, and wherein the means for securing the first fastening means further comprises a first hook and loop fastener pad on the abutting surface of the first pad portion and a complementary hook and loop fastener pad on the complementary abutting surface of the second pad portion, whereby the belt may be secured to the waist of the wearer when the belt is encircling the waist and the abdominal support pad portions are disposed in overlying relationship with one another.

4. The support belt of claim 2, wherein said back support area and said abdominal support area are each of approximately five inches in vertical height and the reduced side areas are each of approximately three inches in vertical height.

5. The support belt of claim 1, the second fastening means further comprising:

a. a first strap hook and loop fastener pad on the strap and disposed inwardly of the fastening means on said one end; and b. a second strap hook and loop fastener pad on the flap and complementary with the first strap hook and loop fastener pad, whereby the flap means is secured to the belt when the belt is encircling the waist of the wearer.

6. The support belt of claim 1, further comprising utility rings secured to the belt at the reduced side areas for securing the belt directly to a harness or implement to be moved or lifted by the wearer that provides an ability to use the trunk of the body to aid in the activity with added safety.

7. A support belt adapted for encircling and being secured to the waist of a wearer for providing both back and abdominal muscle support during strenuous activity while providing a non-interfering fit with the skeletal structure of the ribs and hips of the wearer, the belt comprising:

a. an elongate base having a longitudinal axis and opposite outer ends and made of flexible material to accommodate the various movements of the waist and associated placement of the hips and ribs of the wearer;

b. an enlarged back support area having a first fixed predetermined vertical height and integral within the base such that the area supports the back of the wearer when the belt is encircling the waist of the wearer;

c. an enlarged first abdominal support portion located on one outer end of the base and having a fixed predetermined vertical height substantially the same as the first fixed predetermined vertical height of the back support and positioned to define an abdominal support area opposite the back support area and located in the vicinity of the abdominal wall of the wearer when the belt is encircling the waist;

d. an enlarged second abdominal support portion located on the other outer end of the base and the first abdominal support portion located on one outer end of the base and having a fixed predetermined vertical height coexistent with said first abdominal support height and positioned such that the abdominal support area is diametrically opposite the back support area and is located in the vicinity of the abdominal wall of the wearer when the belt is encircling the waist, said abdominal support portions adapted to be located in overlying relationship with one another when the belt is encircling the waist;

e. reduced side sections of the base having a second predetermined vertical height smaller than said first predetermined vertical height and located on the base intermediately of the areas and opposite one another between the hips and ribs of the wearer when the belt is encircling the waist, said reduced side sections being sized to allow the belt to be sufficiently tightened against both the back and abdominal walls without encountering the skeletal structure of the ribs or hips of the wearer thereby evenly distributing and providing optimum support to both the back and abdominal walls; and f. a first fastening means for releasably securing the base about the waist of the wearer;

g. an elongate strap of flexible, generally non-stretchable material secured to and coaxial with the base, and having free opposite ends; and h. a second, cinchable fastening means on the strap comprising a fastener secured to one of said strap ends and a flap adapted to be received in and secured by said fastener and cinched to fit when the belt is placed around the waist of the wearer.

8. The support belt of claim 7, wherein said second fastening means further comprises:

a. a first strap hook and loop fastener pad on the strap and disposed inwardly of the fastener at said one end; and b. a second strap hook and loop fastener pad on the flap and complementary with the first strap hook and loop fastener pad, whereby the flap may be secured to the belt when the belt is encircling the waist.

9. The support belt of claim 8, wherein the abdominal support portions, when in overlying relationship with one another, have abutting surfaces and wherein the first fastening means further comprises a first hook and loop fastener pad on the abutting surface of one abdominal support portion and a complementary abdominal hook and loop fastener pad on the complementary abutting surface of the other abdominal support portion, whereby the belt may be secured to the waist of the wearer when the belt is encircling the waist and the abdominal support portions are disposed in overlying relationship with one another.

10. The support belt of claim 8, further comprising utility rings secured to the belt at the reduced side sections for securing the belt directly to a harness or implement to be moved or lifted by the wearer that provides an ability to use the trunk of the body to aid in the activity with added safety.

11. The support belt of claim 8, wherein said back support area and said abdominal support areas are each of approximately five inches in vertical height and the reduced side portions are each of approximately three inches in vertical height.

* * * * *